(12) United States Patent
Dagan et al.

(10) Patent No.: US 8,580,256 B2
(45) Date of Patent: Nov. 12, 2013

(54) STABILIZED ANTI-HEPATITIS B (HBV) ANTIBODY FORMULATIONS

(75) Inventors: Shlomo Dagan, Nes Ziona (IL); Rachel Eren, Moshav Netaim (IL); Hemant Kumar Misra, Shrewsbury, MA (US); Walter G. Gowan, Jr., Pelham, AL (US); Sandra O'Connor, Mount Vernon, NH (US)

(73) Assignee: Yeda Reseach and Development Company Limited (IL)

( * ) Notice: Subject to any disclaimer, the term of this patent is extended or adjusted under 35 U.S.C. 154(b) by 182 days.

(21) Appl. No.: 12/821,593

(22) Filed: Jun. 23, 2010

(65) Prior Publication Data

US 2010/0330099 A1 Dec. 30, 2010

Related U.S. Application Data

(62) Division of application No. 11/911,939, filed as application No. PCT/US2005/013151 on Apr. 18, 2005, now Pat. No. 7,785,595.

(51) Int. Cl.
*A61K 39/395* (2006.01)

(52) U.S. Cl.
USPC ............ 424/130.1; 424/159.1; 424/161.1

(58) Field of Classification Search
None
See application file for complete search history.

(56) References Cited

U.S. PATENT DOCUMENTS

| | | | |
|---|---|---|---|
| 5,061,641 A | 10/1991 | Shochat et al. | |
| 6,019,968 A | 2/2000 | Platz et al. | |
| 6,171,586 B1 | 1/2001 | Lam et al. | |
| 7,060,268 B2 | 6/2006 | Andya et al. | |
| 2004/0109854 A1 | 6/2004 | Lee et al. | |
| 2005/0002937 A1 | 1/2005 | Giles-Komar et al. | |
| 2005/0142139 A1* | 6/2005 | Schulke et al. | 424/178.1 |
| 2008/0286280 A1 | 11/2008 | Kallmeyer et al. | |

FOREIGN PATENT DOCUMENTS

| | | |
|---|---|---|
| AU | 735411 B2 | 6/1998 |
| EP | 0852941 A1 | 7/1998 |
| EP | 0852951 A1 | 7/1998 |
| WO | 8911298 A1 | 11/1989 |
| WO | 9747653 | 12/1997 |
| WO | 9747654 | 12/1997 |
| WO | 9822136 A2 | 5/1998 |
| WO | 0212500 A2 | 2/2002 |
| WO | WO 03/028722 | 4/2003 |
| WO | WO 2004/091658 | 10/2004 |

OTHER PUBLICATIONS

Wang. Lyophilization and development of solid protein pharmaceuticals. Int J Pharm. Aug. 10, 2000;203(1-2):1-60.*
Galun et al. Clinical evaluation (phase I) of a combination of two human monoclonal antibodies to HBV: safety and antiviral properties. Hepatology. Mar. 2002;35(3):673-9. Erratum in: Hepatology Apr. 2002;35(4):986.
El-Serag, H., et al, "Rising Incidence of Hepatocellular Carcinoma in the United States," New England Journal of Medicine, (1999) 340(10): 745-750.
Rosen, Hugo, et al., "Viral Hepatitis in the Liver Transplant Recipient," Infectious Disease Clinics of North America, (2000) 14(3): 761-785.
International Search Report for PCT IL97/00183, (1997).
International Search Report for PCT IL97/00184, (1997).
Eren et al (2000) Hepatology. 32:588-596.
International Search Report and the Written Opinion of the International Searching Authority dated Dec. 28, 2005 for PCT/US2005/013151.

* cited by examiner

*Primary Examiner* — Michelle S Horning
(74) *Attorney, Agent, or Firm* — Cantor Colburn LLP

(57) ABSTRACT

The present invention provides liquid formulations of antibodies or fragments thereof that specifically bind to a hepatitis B virus (HBV) antigen, which formulations exhibit stability, low to undetectable levels of aggregations, and very little to no loss of the biological activities of the antibodies or antibody fragments, even during long periods of storage. Furthermore, the invention provides methods of preventing, treating or ameliorating one or more symptoms associated with HBV infection utilizing the liquid formulations of the present invention.

11 Claims, 2 Drawing Sheets

1 - AB 17 & AB19, 4°C, 2 µg/lane
2 - AB 17 & AB19, 25°C, 2 µg/lane
3 - AB 17 & AB19, 40°C, 2 µg/lane 1 - AB 17 & AB19, 4°C, 2 µg/lane
2 - AB 17 & AB19, 25°C, 2 µg/lane
3 - AB 17 & AB19, 40°C, 2 µg/lane

SEQUENCE LISTING

<160> NUMBER OF SEQ ID NOS: 4

<210> SEQ ID NO 1
<211> LENGTH: 109
<212> TYPE: PRT
<213> ORGANISM: Homo sapiens

<400> SEQUENCE: 1

Ser Tyr Val Leu Thr Gln Pro Pro Ser Val Ser Val Ala Pro Gly Lys
 1               5                  10                  15

Thr Ala Arg Ile Ser Cys Gly Gly Asn Asn Ile Gly Thr Lys Asn Val
             20                  25                  30

His Trp Tyr Gln Gln Lys Pro Gly Gln Ala Pro Val Leu Val Val Tyr
         35                  40                  45

Ala Asp Ser Asp Arg Pro Ser Gly Ile Pro Glu Arg Phe Ser Gly Ser
     50                  55                  60

Asn Ser Gly Asn Thr Ala Thr Leu Thr Ile Ser Arg Val Glu Val Gly
 65                  70                  75                  80

Asp Glu Ala Asp Tyr Tyr Cys Gln Val Trp Asp Ser Val Ser Tyr His
                 85                  90                  95

Val Val Phe Gly Gly Gly Thr Thr Leu Thr Val Leu Gly
            100                 105

<210> SEQ ID NO 2
<211> LENGTH: 121
<212> TYPE: PRT
<213> ORGANISM: Homo sapiens

<400> SEQUENCE: 2

Gln Val Gln Leu Val Glu Ser Gly Gly Val Val Gln Pro Gly Gly
 1               5                  10                  15

Ser Leu Arg Leu Ser Cys Ala Pro Ser Gly Phe Val Phe Arg Ser Tyr
             20                  25                  30

Gly Met His Trp Val Arg Gln Thr Pro Gly Lys Gly Leu Glu Trp Val
         35                  40                  45

Ser Leu Ile Trp His Asp Gly Ser Asn Arg Phe Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Met Tyr Phe Cys
                 85                  90                  95

Ala Arg Glu Arg Leu Ile Ala Pro Ala Ala Phe Asp Leu Trp Gly
            100                 105                 110

Gln Gly Thr Leu Val Thr Val Ser Ser
            115                 120

<210> SEQ ID NO 3
<211> LENGTH: 112
<212> TYPE: PRT
<213> ORGANISM: Homo sapiens

<400> SEQUENCE: 3

Asp Ile Val Met Thr Gln Ser Pro Leu Ser Leu Ser Val Thr Pro Gly
 1               5                  10                  15

Glu Pro Ala Ser Ile Ser Cys Arg Ser Ser Gln Ser Leu Leu His Arg
             20                  25                  30

-continued

```
Ser Gly Asn Asn Tyr Leu Asp Trp Tyr Leu Gln Lys Pro Gly His Ser
            35                  40                  45

Pro Gln Leu Leu Ile Tyr Val Gly Ser Asn Arg Ala Ser Gly Val Pro
        50                  55                  60

Asp Arg Phe Ser Gly Ser Gly Ser Gly Thr Glu Tyr Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Arg Thr Phe Gly Gln Gly Thr Lys Leu Glu Ile Lys
            100                 105                 110

<210> SEQ ID NO 4
<211> LENGTH: 129
<212> TYPE: PRT
<213> ORGANISM: Homo sapiens

<400> SEQUENCE: 4

Gln Val Gln Leu Val Glu Ser Gly Gly Val Val Arg Pro Gly Arg
1               5                   10                  15

Ser Leu Arg Leu Ser Cys Ala Ala Ser Gly Phe Ala Phe Ser Asp Tyr
                20                  25                  30

Ser Ile Asn Trp Val Arg Gln Ala Pro Gly Lys Gly Leu Glu Trp Val
            35                  40                  45

Ala Ile Ile Ser Tyr Asp Gly Arg Ile Thr Tyr Tyr Arg Asp Ser Val
        50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Gln Tyr Tyr Asp Phe Trp Ser Gly Ser Ser Val Gly Arg Asn
            100                 105                 110

Tyr Asp Gly Met Asp Val Trp Gly Leu Gly Thr Thr Val Thr Val Ser
        115                 120                 125

Ser
```

STABILIZED ANTI-HEPATITIS B (HBV) ANTIBODY FORMULATIONS

CROSS REFERENCE TO RELATED APPLICATIONS

This application is a Divisional of U.S. Patent Application No. 11/911,939 filed on Oct. 18, 2007, the entire content of which is herein incorporated by reference in its entirety, which said U.S. Application No. 11/911,939 is the U.S. National Phase of PCT/2005/013151 filed on Apr, 18, 2005, the entire content of which is herein incorporated by reference in its entirety.

FIELD OF THE INVENTION

The present invention concerns a liquid formulation of anti HBsAg human monoclonal antibodies for the treatment or prevention of hepatitis B infection.

BACKGROUND OF THE INVENTION

Infection with hepatitis B virus (HBV) is a global public health problem, with a mortality rate that places it among the top 10 major infectious killers. The World Health Organization estimates that 400 million people are carriers of the virus worldwide. It has been estimated that acute HBV disease leads to 600,000 deaths annually; complications of chronic disease, including HBV-induced liver cirrhosis and hepatocellular carcinoma, account for about 400,000 deaths per year (El-Serag H B and Mason A C. *N Engl J Med* 1999; 340 (10):745-750).

Many patients who are infected by the hepatitis B virus are unable to resolve the infection and develop chronic HBV, which may lead to deterioration of liver function, including cirrhosis and hepatic decompensation and a subsequent need for transplantation. Although the infected liver is removed before transplantation, some circulating virus still remains in the serum, and other reservoirs are believed to exist in other body compartments. Therefore, these patients are at high risk of HBV-reinfection of their transplanted liver.

Prevention of HBV infection may be achieved with active or passive immunization. Active immunization with recombinant HBV vaccines can prevent HBV infection if given before exposure. These vaccines, made from noninfectious viral subunits, have been shown to be safe and effective and confer long-term immunity.

Passive immunization with hepatitis B specific antibodies, given shortly after exposure, can decrease the incidence or severity of disease. Hepatitis B immune globulin (HBIG) is a plasma-derived, polyclonal preparation of antibodies to the hepatitis B surface antigen (anti-HBs). The antibodies bind to hepatitis surface antigen on the surface of the virus and neutralize it, thus preventing infection.

Passive immunization with HBIG is most effective if given when viral titers are low and an excess of antibody can be achieved. For this reason, HBIG has been effective in preventing new infections. It also appears to be partially effective when used to prevent reinfection after liver transplantation, where the viral load is decreased by removal of the infected organ. It has been especially effective in patients with low viral titers before surgery.

At present, there are three antiviral products available for treatment of chronic hepatitis B: interferon 2b (INTRON® A, Schering), lamivudine (EPIVIR HBV®, GlaxoSmithKline), and/or adefovir dipivoxil (HEPSERA™, Gilead Sciences). However, there is no therapy to cure chronic HBV infections in all patients. HBIG has not been effective in treating patients with chronic hepatitis B where persistent levels of virus are produced, and it is not possible to produce antibody excess without frequent administrations of antibody. End-stage liver disease related to chronic viral hepatitis is the leading indication for orthotopic liver transplantation (OLT) worldwide. The term "orthotopic" means that the diseased organ is removed and the new allograft is implanted in the normal or usual position in the right upper quadrant of the abdomen. OLT for cirrhosis and organ failure due to HBV infections accounts for 5% to 10% of all adult transplants. Protection of the transplanted liver from recurrent HBV infection is critical to preserving graft function. Life-long HBV prophylactic treatment is probably necessary, since virus remains in several other body compartments (spleen, lymph nodes, kidneys, skin, gastrointestinal tract, gonads, nerve ganglia, and brain) following removal of the infected liver. Hepatitis B infection of the liver reoccurs rapidly when the patient is immunosuppressed after transplantation, resulting in progressive disease, graft failure, and death. Patients with signs of active HBV replication (HBeAg and/or high levels of HBV DNA) at the time of transplantation are at increased risk. Disease recurrence occurs even more quickly after repeat transplantation (Rosen HR and Martin P. Infectious Disease Clinics of North America. September 2002; 14 (3):761-786). Overall, the use of plasma-derived polyclonal antibodies is limited because these preparations have variable activity, limited availability and there are potential hazards for the transmission of infectious agents.

In contrast, monoclonal antibodies (mAbs) can be consistently produced and do not carry the infectious risks associated with plasma-derived products.

In previous studies two fully human monoclonal antibodies were developed directed against different epitopes of hepatitis B surface antigen (HBsAg) (PCT/IL97/00184 and PCT/IL97/00183). A single administration of a mixture of these antibodies into HBV chronic carrier chimpanzees resulted in immediate reduction in HBsAg levels followed by a recurrence to initial levels within a few days (Eren et al., 2000 *Hepatology* 32, 588-596).

A phase 1 clinical study was conducted using a mixture of these two monoclonal antibodies (termed HBV-AB$^{xTL}$ and now HEPEX B™). In part A of the study patients received a single intravenous (IV) infusion of antibodies while in part B patients received 4 weekly infusions. The antibody mixture was effective in reducing HBsAg and HBV DNA levels.

HEPEX B™ for IV use was initially prepared as two separate liquid formulations for each of the antibodies (17 and 19) in phosphate buffered saline (65 mM sodium phosphate, 80 mM sodium chloride, at pH 7.0). The two mabs were mixed together prior to administration in a ratio of approximately 1:1 international units.

A need exists to develop a high dosage liquid formulation of HEPEX B that would be suitable for subcutaneous as well as intra-muscular administration. The prior liquid antibody preparations have short shelf lives and may lose biological activity of the antibodies resulting from chemical and physical instabilities during the storage. Thus, there is a need for a stable liquid formulation for an anti-HBV antibody effective to prevent HBV infection.

SUMMARY OF INVENTION

The present invention is based, in part, on the development of high concentration liquid formulations of antibodies or fragments thereof that specifically bind to an HBV antigen, which formulations exhibit, in the absence of inorganic salts but in the presence of amino acids, a carbohydrate and a surfactant, stability and low to undetectable levels of antibody fragmentation and/or aggregation, and very little to no loss of biological activities of the antibody or antibody fragment during manufacture, preparation, transportation, and storage. The liquid formulations of the present invention facilitate the administration of antibodies or fragments thereof that specifically bind to an HBV antigen for the prevention, treatment, management and/or amelioration of an HBV infection, or one or more symptoms thereof. In particular, the liquid formulations of the present invention enable to quickly administer a sterile dosage of antibodies or fragments thereof that specifically bind to an HBV antigen without having to accurately and aseptically mix the two separate antibodies (17 and 19) or antibody fragments prior to administration as required for the previously used dosage form.

The present invention provides liquid formulations of anti-HBV antibodies or fragments thereof substantially free of inorganic salts, said formulations comprising an amino acid, organic salt, surfactant, a carbohydrate and a concentration of about 10 mg/ml or higher of an antibody or a fragment thereof that specifically binds to an HBV antigen said formulations having a pH range of about 5.0 to about 7.5, preferably about 6.5.

The present invention encompasses stable liquid formulations of an antibody or a fragment thereof that specifically binds to an HBV antigen, which formulations exhibit low to undetectable levels of antibody aggregation and/or fragmentation with very little or no loss of the biological activities of the antibody or antibody fragment during manufacture, preparation, transportation, and long periods of storage. The present invention also encompasses stable liquid formulations of an antibody or fragment thereof that specifically binds to an HBV antigen, said antibody or antibody fragment comprising a variable heavy (VH) and variable light (VL) domain having the amino acid sequence of any VH and VL domain shown in FIG. 1, and said formulations exhibiting low to undetectable levels of antibody aggregation and/or fragmentation, and very little to no loss of the biological activities of the antibodies or antibody fragments.

Figure 1:
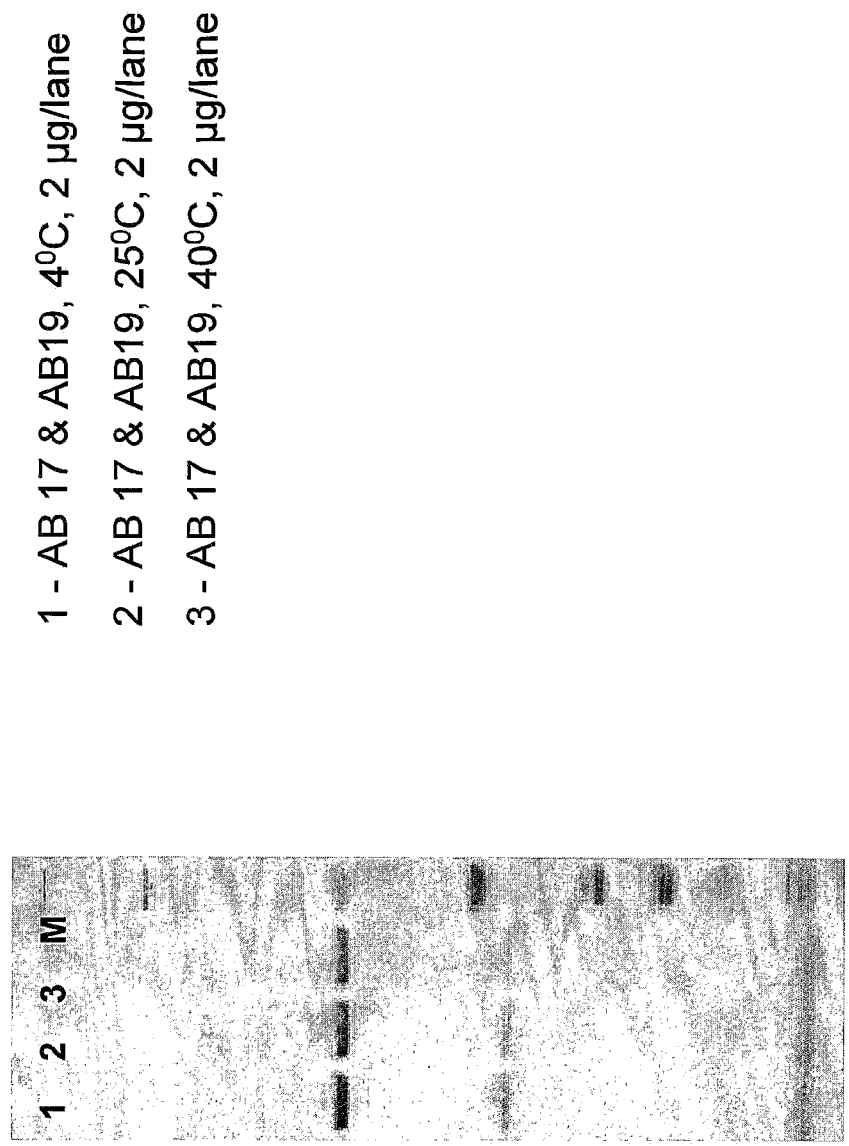
FIG. 1 Reduced SDS-PAGE with Commassie Bluestaining of AB 17+AB 19 combination samples in formulation 3 containing 0.1% T80 at 4° C., 25° C. and 40° C. Heavy and lightchains are observed in the gel.
Figure 2:
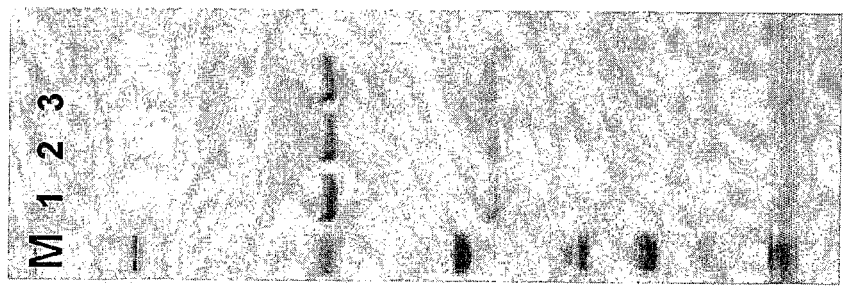
FIG. 2 Reduced SDS-PAGE with Commassie Blue staining of AB 17+AB 19 combination samples in formulation 3 containing 0.01% T80 at 4° C., 25° C. and 40° C. Heavy and light chains are observed in the gel.

The present invention encompasses liquid formulations of antibodies or fragments thereof that specifically bind to an HBV antigen, said formulations having stability at 4° C. as assessed by measuring specific activity (using an immuno assay), integrity and purity (using SDS PAGE, and high performance size exclusion chromatography (HPSEC)) appearance (visual inspection) and protein concentration for at least 3 months. The present invention also encompasses liquid formulations of antibodies or fragments thereof that specifically bind to an HBV antigen, said formulations having low to undetectable levels of antibody aggregation as measured by HPSEC, and further, exhibit very little to no loss of the biological activity of the antibodies or antibody fragments of the formulation compared to the reference antibodies as measured by antibody binding assays such as e.g., ELISA.

The present invention provides methods for preparing liquid formulations of an antibody or fragment thereof that specifically binds to an HBV antigen, said methods comprising concentrating a fraction containing the purified antibody or antibody fragment to a final concentration of about 10 mg/ml, about 20 mg/ml, about 30 mg/ml, about 40 mg/ml, about 50 mg/ml, about 60 mg/ml, about 70 mg/ml, about 80 mg/ml, about 90 mg/ml, about 100 mg/ml, about 200 mg/ml, about 250 mg/ml, or about 300 mg/ml using a semi-permeable membrane with an appropriate molecular weight cutoff (e.g. a 30 kD cutoff for whole antibody molecules and $F(ab')_2$ fragments, and a 10 kD cutoff for antibody fragments such as a Fab fragment), and filtering the concentrated antibody or antibody fragment fraction into the formulation buffer using the same membrane.

The formulation buffer of the present invention comprises alanine at a concentration ranging from about 10 mM to about 100 mM, or about 85 mM to about 95 mM, and is most preferably 90 mM.

The formulation of the present invention further comprises sodium citrate at a concentration ranging from 10 mM to about 30 mM, or about 15 mM to about 25 mM, and is most preferably 20 mM.

The formulation of the present invention further comprises TWEEN (polysorbate) 80 at a concentration ranging from about 0.05% to about 0.5%, and is most preferably about 0.1%. The formulation of the present invention further comprises trehalose at a concentration ranging from about 1% to about 5%, or about 2% to 4%, and is most preferably 3%. The liquid formulations of the present invention are prepared by maintaining the antibodies in an aqueous solution at any time during the preparation. In other words, the liquid formulations are prepared without involving any step of drying the antibodies or the formulations themselves by, for example, lyophilization, vacuum drying, etc.

The liquid formulations of the present invention may be sterilized by sterile filtration using a 0.2 micron filter. Sterilized liquid formulations of the present invention may be administered to a subject to prevent, treat, manage or ameliorate an HBV infection or one or more symptoms thereof.

The present invention also provides kits comprising the liquid formulations of antibodies or fragments thereof that specifically bind to an HBV antigen for use by, e.g., a healthcare professional or the patient. The present invention further provides methods of preventing, treating, managing or ameliorating an HBV infection or one or more symptoms thereof, by administering the liquid formulations of the present invention.

It is understood that antibodies and antibody fragments also include, Fab fragments, Fv fragments, single chain antibodies, diabodies and other binding molecules that may be synthesized or produced based on the binding properties or CDRs of the antibodies described herein.

The invention is further summarized as follows:
1. An antibody formulation comprising:
   (a) at least 10 mg/ml of one or more antibodies, or fragments thereof that specifically bind to an HBV antigen;
   (b) alanine;
   (c) sodium citrate;
   (d) TWEEN (polysorbate) 80; and
   (e) trehalose in an aqueous carrier, wherein at least one of said antibodies or antibody fragments is Mab17 or Mab19.
2. The formulation of claim 1, wherein the aqueous carrier is distilled water.
3. The formulation of claim 1, wherein the formulation is sterile.
4. The formulation of claim 1, wherein the formulation is homogenous.
5. The formulation of claim 1, wherein the formulation has a pH in the range between about 5.0 to 7.5.

6. The formulation of claim 1, wherein at least one of the antibodies or antibody fragments is at a concentration of at least 20 mg/ml.
7. The formulation of claim 1, wherein at least one of the antibodies or antibody fragments is at a concentration of at least 40 mg/ml.
8. The formulation of claim 7, wherein at least one of the antibodies or antibody fragments is at a concentration of at least 80 mg/ml.
9. The formulation of claim 8, wherein at least one of the antibodies or antibody fragments is at a concentration of at least 100 mg/ml.
10. The formulation of claim 1, wherein alanine is at concentration of about 85 to about 95 mM.
11. The formulation of claim 1, wherein alanine is at concentration of about 90 mM.
12. The formulation of claim 1, wherein sodium citrate is at concentration of about 10 to about 30 mM.
13. The formulation of claim 1, wherein sodium citrate is at concentration of about 20 mM.
14. The formulation of claim 1, wherein TWEEN (polysorbate) 80 is at concentration of about 0.05% to about 0.5%.
15. The formulation of claim 1, wherein TWEEN (polysorbate) 80 is at concentration of about 0.1%.
16. The formulation of claim 1, wherein trehalose is at concentration of about 1% to about 10%.
17. The formulation of claim 1, wherein trehalose is at concentration of about 3%.
18. The formulation of claim 1, wherein at least one of the antibodies or antibody fragments that specifically binds to an HBV antigen is stable at room temperature for at least 6 months as determined by HPSEC.
19. The formulation of claim 1, wherein at least one of the antibodies or antibody fragments that specifically binds to an HBV antigen is stable at 4° C. for at least 2 years as determined by HPSEC.
20. The formulation of claim 1, wherein less than 10% of the antibodies or antibody fragments form an aggregate as measured by HPSEC.
21. The formulation of claim 1, wherein less than 5% of the antibodies or antibody fragments form an aggregate as measured by HPSEC.
22. The formulation of claim 1, wherein at least one of said antibodies or antibody fragments comprises a variable light (VL) domain having the amino acid sequence of SEQ ID NO. 1 and a variable heavy (VH) domain having the amino acid sequence of SEQ ID NO. 2; and at least a second of said antibodies or antibody fragments comprises a variable light (VL) domain having the amino acid sequence of SEQ ID NO. 3 and a variable heavy (VH) domain having the amino acid sequence of SEQ ID NO. 4.
23. A pharmaceutical unit dosage form suitable for parenteral administration to a human which comprises an antibody formulation of claim 1 or 22 in a pharmaceutically suitable container.
24. The pharmaceutical unit dosage form of claim 23, wherein at least one of the said antibodies or fragments thereof has a concentration of from about 10 mg/ml to about 100 mg/ml in a volume of from 1 ml to 20 ml.
25. The pharmaceutical unit dosage form of claim 23, wherein said antibody or a fragment thereof has a concentration of 80 mg/ml in a volume of 1 ml.
26. The pharmaceutical unit dosage-form of claim 23, wherein said antibody formulation is suitable for subcutaneous administration.
27. The pharmaceutical unit dosage-form of claim 23, wherein said antibody formulation is suitable for intravenous administration.
28. The pharmaceutical unit dosage-form of claim 23, wherein said antibody formulation is suitable for intramuscular administration.
29. A sealed container comprising a formulation of claim 1.
30. A method for the treatment of HBV infections in a subject, said method comprising administering a prophylactically or therapeutically effective amount of the formulation of claim 1.
31. A method for reducing HBV infection of a transplanted liver comprising administering to an individual in need thereof the formulation of claim 1.
32. A method for treating an individual born to an HBV infected mother, comprising administering to said individual the formulation of claim 1.
33. A method for treating a healthcare worker exposed to HBV, comprising administering the formulation of claim 1 to said healthcare worker.
34. The method of claim 30, 31, 32 or 33, wherein the formulation is administered parenterally.
35. The method of claim 30, 31, 32 or 33, wherein the formulation is administered intramuscularly.
36. The method of claim 30, 31, 32 or 33, wherein the formulation is administered intravenously.
37. The method of claim 30, 31, 32 or 33, wherein the formulation is administered subcutaneously.
38. A formulation comprising:
    (a) at least 10 mg/ml of at least two antibodies, or fragments thereof that specifically bind to an HBV antigen;
    (b) an amino acid;
    (c) a buffer;
    (d) a surfactant; and
    (e) a sugar
    in an aqueous carrier, wherein the at least two antibodies or antibody fragments are selected from the group consisting of Mab 17, Mab 19 and fragments thereof.
39. The formulation of claim 38 wherein: (a) the amino acid includes at least one of alanine;
    (b) the buffer is a citrate buffer;
    (c) the surfactant includes at least one of PEG-3350, PEG-4000 (1%), TWEEN (polysorbate) 20 or TWEEN 80 (0.1%); and
    (d) the sugar includes at least one of Lactose, Mannose, Mannitol, Sorbitol, Sucrose or Trehalose, in an aqueous carrier, wherein the at least two antibodies or antibody fragments are selected from the group consisting of Mab 17 and Mab 19 and fragments thereof.
40. The formulation of claim 1 or 38, wherein said fragments bind to one or more portions or fragments of HPV wherein said binding is effective to inhibit HPV infection in a subject.

DETAILED DESCRIPTION OF THE INVENTION

Methods

Amino Acid Sequences of VL and VH Domains of AB 19 and AB 17

```
AB 19 VL
                                         (SEQ ID NO. 1)
SYVLTQPPSV SVAPGKTARI SCGGNNIGTK NVHWYQQKPG

QAPVLVVYAD SDRPSGIPER FSGSNSGNTA TLTISRVEVG

DEADYYCQVW DSVSYHVVFG GGTTLTVLG
```

```
AB 19 VH
                                       (SEQ ID NO. 2)
QVQLVESGGG VVQPGGSLRL SCAPSGFVFR SYGMHWVRQT

PGKGLEWVSL IWHDGSNRFY ADSVKGRFTI SRDNSKNTLY

LQMNSLRAED TAMYFCARER LIAAPAAFDL WGQGTLVTVS

S

AB 17 VL
                                       (SEQ ID NO. 3)
DIVMTQSPLS LSVTPGEPAS ISCRSSQSLL HRSGNNYLDW

YLQKPGHSPQ LLIYVGSNRA SGVPDRFSGS GSGTEYTLKI

SRVEAEDVGV YYCMQALQTP RTFGQGTKLE IK

AB 17 VH
                                       (SEQ ID NO. 4)
QVQLVESGGG VVRPGRSLRL SCAASGFAFS DYSINWVRQA

PGKGLEWVAI ISYDGRITYY RDSVKGRFTI SRDDSKNTLY

LQMNSLRTED TAVYYCARQY YDFWSGSSVG RNYDGMDVWG

LGTTVTVSS
```

In order to determine the formulation that would provide a high degree of stability to antibodies AB 17 and AB 19, different excipients were tested by profiling the antibodies' structural stability while undergoing changes (over time and pH) and exposure to stressful conditions (e.g. shear stress and slow freeze-thaw cycles) including accelerated stability studies via incubation at 50° C. for one- to two-weeks. At several time points (e.g. $t_0$, $t_7$, $t_{14}$) the stability of the molecules was examined with and without stress using the following tools: Right Angle Light Scatter (RALS), Intrinsic and Extrinsic Fluorescence (IF, EF) in conjunction with analytical methods like High-Performance Size Exclusion Chromatography (HP-SEC).

RALS is employed to detect and monitor the subtle changes in the associative behavior of the molecule, which can result in aggregation and/or precipitation. RALS monitors macroscopic changes as a soluble molecule transitions to insoluble aggregates. The IF assay measures stress-induced conformational changes in proteins as observed by changes in the Tryptophan environment. EF utilizes an external, non-covalent, polarity-sensitive fluorescent probe to examine a protein's apparent exposure of hydrophobic clefts and to monitor possible changes in this parameter as a function of various environmental stresses and conditions.

Slow Freeze-Thaw

After reading initial RALS or turbidity, approximately 400~μL of sample was frozen slowly in an Eppendorf tube by placing it in a −80° C. freezer. After freezing was complete (minimum of four hours), all samples were thawed on the bench top (room temperature). The process was repeated for a total of 5 cycles.

Shear Stress

750~μL, of the tested formulation were shear stressed in a conical glass vial using a triangular stir bar. The samples were spun at 300 rpm (no cavitation) for 24 hours before removal from the magnetic stirrer for analysis.

SDS-Page

Sodium dodecyl sulphate Poly Acrylamide gel electrophoresis (SDS-PAGE) was performed using Bis-Tris gradient of 4-12%.

2 μg of the antibody combination were mixed with a native sample buffer (InvitroGen) containing 50 mM DTT and incubated for 10 min at 100° C. prior to loading.

The gels were run at 200V for about 30 min, and then rinsed twice in DDW for 3 min. The gels were then stained with Coomasie Blue (Gelcode; Pierce) while shaking for one hour, and then rinsed in DDW over night.

Photographs of the gels were taken using the Lis-cap program in a Renium camera

EXAMPLE 1

This example describes the selection of excipients for a liquid formulation comprising the human anti HBsAg antibodies AB 19 and AB 17, AB 19 having the amino acid sequence AB 19 VL (Light chain; SEQ ID NO.1) and AB 19 VH (Heavy chain; SEQ ID NO.2) and AB 17 having the amino acid sequence AB 17 VL (Light chain; SEQ ID NO.3) and AB 17 VH (Heavy chain; SEQ ID NO.4).

AB 19 and AB 17 may be produced by hybridoma cells (deposited at the ECACC under accession nos. 96052169 and 96052168), or may be prepared by recombinant methods well known in the art, e.g. by CHO expression systems transfected with the genes encoding the heavy and light chain of each antibody.

Buffer Selection

Several pH values for the formulation were compared ranging from 5.0 to 7.5 generated using different buffers: Sodium Citrate, Histidine or Succinic acid. AB 17 and AB 19 in the different buffers were examined by IF, RALS, EF and SEC-HPLC under different conditions: incubation at 50° C. for seven and fourteen days, exposure to shear stress and slow freeze-thaw cycles.

The formulation containing Citrate at pH 6.5 performed best in the assays and therefore Sodium Citrate was chosen as the preferred buffer for the formulation.

Evaluation of Amino Acids as Stabilizers

Using Sodium Citrate as a buffer, a set of formulations containing different amino acids at a concentration of 50 mM was generated.

These formulations were examined by IF, RALS, EF and SEC-HPLC, and were subjected to shear stress and slow freeze-thaw cycles.

The formulations containing Glutamic acid and Proline scored highest, followed by the formulation containing Alanine.

These three amino acids were further analyzed in order to establish the feasibility of concentrating the antibodies to 100 mg/ml.

The formulation containing Alanine scored best in the concentration studies. Since Glutamic acid had scored best in the previous study, these two amino acids were chosen as the preferred amino acid stabilizers and were reexamined in a combination study including additional formulation excipients as will be described below.

Evaluation of Carbohydrates and Surfactants as Stabilizers

Carbohydrates are typically used as stabilizers, isotonic adjusters, and/or bulking agents (in the case of lyophilization). Surfactants are typically used to protect proteins against shear stress. Several formulations were generated containing each 20 mM Sodium Citrate, 50 mM Glutamic acid and a different carbohydrate or surfactant. The following excipients were examined: Lactose, Mannose, Mannitol, Sorbitol, Sucrose and Trehalose (3%), PEG-3350 and PEG-4000 (1%), TWEEN (polysorbate) 20and TWEEN 80 (0.1%).

All formulations were examined by IF, RALS, EF and SEC-HPLC and were stressed by shear stress and slow freeze-thaw.

The formulations containing Trehalose and Sorbitol scored the best over time. Therefore both of these carbohydrates were chosen as preferred carbohydrates for the antibody formulation and would be further examined in the Combination study.

The formulation containing TWEEN (polysorbate) 80 (T80) scored best among the surfactants and therefore T80 was chosen as the preferred surfactant for the antibody formulation.

Finally, based on the data described above several formulations of the antibodies were prepared examining different combinations of stabilizing excipients in order to determine the preferred combination. These combinations were tested by IF, RALS, EF and SEC-HPLC.

These assays indicated that Sodium Citrate at pH 6.5 provided the greatest stability to AB 17 and AB 19. The amino acids Alanine and Glutamic acid were identified as lead stabilizers for AB 17 and AB 19, and Trehalose was selected over the other strong carbohydrate stabilizer, Sorbitol. The surfactant, TWEEN (polysorbate) 80, was found to reduce the shear stress of the molecule.

Based on these findings four liquid formulations containing the preferred excipients were evaluated for selection of a preferred clinical formulation for use in treatment or prevention of HBV infections. The formulations were as shown in Table 1 below.

TABLE 1

Matrix of formulations prepared for this study

| Formulation no. | Na Citrate (mM) | Alanine (mM) | T80 (%) | Trehalose (%) |
|---|---|---|---|---|
| 1 | 20 | 20 | 0.1 | 5 |
| 2 | 20 | 50 | 0.1 | 4 |
| 3 | 20 | 90 | 0.1 | 3 |
| 4 | 20 | 20 | 0.05 | 5 |

These formulations were again examined using the assays described above. Under subjection to temperature, shear and freeze-thaw stress, all formulations maintained both high purities and recoveries. Overall, Formulation 3 performed slightly better over a 28 day stability study. This suggests that a higher Alanine concentration may help to stabilize the antibodies.

EXAMPLE 2

Preparation of AB 17 Formulation

The stock of AB 17 (in PBS) was diluted 1:1 prior to concentrating with a solution of 20 mM Sodium Citrate, 50 mM Alanine and 100 mM NaCl in order to provide stability while concentrating. The protein was then concentrated to ~89 mg/ml by Tangential-Flow Filtration (TFF) over the course of 4 days. The concentrated AB 17 was slightly cloudy, and there was an 80% recovery from the TFF.

The antibody was buffer exchanged using dialysis tubing (MW cutoff=25,000) into the preferred formulation as described above.

EXAMPLE 3

This example describes the stability tests performed on the combination of antibodies AB 17 and AB 19 in formulation 3. Stability studies were performed on samples stored under controlled temperatures at 5° C., 25° C. and 40° C.

Combination samples were prepared containing 90 mg/ml of AB 17+30 mg/m of AB 19 in 2 ml (final concentration 60 mg/m1) in formulation 3 containing either 0.1% TWEEN (polysorbate) 80 or 0.01% TWEEN 80. The samples were subjected to SDS-PAGE under reduced conditions in order to check the purity of the sample and the presence of degradation products. FIGS. 1 and 2 show antibody samples after incubation for 4 weeks in different storage temperatures (FIG. 1: formulation 3 containing 0.1% T80; FIG. 2: formulation 3 containing 0.01% T80). The antibody chains remain intact in all temperatures measured as can be seen by the two distinct bands representing each the heavy and light antibody chains. No impurities and no degradation products were detected. Both TWEEN 80 concentrations tested (0.1% and 0.01%) were effective in stabilizing the antibodies.

A functional property of the antibodies, i.e. binding to HBsAg was measured using an immuno assay and is shown in Table 2. The specific activity (IU/mg) was measured at Time 0 (T0) at the beginning of the incubation and compared with the specific activity 4 weeks (T4) after incubation in different temperatures. As can be seen in Table 2 the specific activity of the antibodies was not significantly changed after 4 weeks incubation, providing another indication to their stability in the tested formulations.

TABLE 2

| Temperature | Formulation 3 + 0.1% T80 $T_0$ (IU/mg) | Formulation 3 + 0.1% T80 $T_4$ (IU/mg) | Formulation 3 + 0.01% T80 $T_0$ (IU/mg) | Formulation 3 + 0.01% T80 $T_4$ (IU/mg) |
|---|---|---|---|---|
| 5° C. | 919.5 | 853.3 | 786 | 863.6 |
| 25° C. | 919.5 | 909.5 | 786 | 883.74 |
| 40° C. | 919.5 | 886.4 | 786 | 745.76 |

EXAMPLES 5-33

Further examples were made as described above according to the following formulations and kept at 5, 25 and 40 degrees Celsius:

| Example | mAb | Conc. (mg/mL) | Formulation | % Tween 80 | % Trehalose | Molar Ratio Tre:mAb |
|---|---|---|---|---|---|---|
| 5 | 17 | 30 mg/ml | 20 mM NaCitrate, 90 mM Alanine, 3% Trehalose, 0.1% Tween 80 | 0.1 | 3 | 395 |
| 6 | 17 | 30 mg/ml | 20 mM NaCitrate, 90 mM Alanine, 3% Trehalose, 0.01% Tween 80 | 0.01 | 3 | 395 |
| 7 | 17 | 60 mg/ml | 20 mM NaCitrate, 90 mM Alanine, 3% Trehalose, 0.1% Tween 80 | 0.1 | 3 | 198 |

-continued

| Example | mAb | Conc. (mg/mL) | Formulation | % Tween 80 | % Trehalose | Molar Ratio Tre:mAb |
|---|---|---|---|---|---|---|
| 8 | 17 | 60 mg/ml | 20 mM NaCitrate, 90 mM Alanine, 3% Trehalose, 0.01% Tween 80 | 0.01 | 3 | 198 |
| 9 | 17 | 90 mg/ml | 20 mM NaCitrate, 90 mM Alanine, 3% Trehalose, 0.1% Tween 80 | 0.1 | 3 | 132 |
| 10 | 17 | 90 mg/ml | 20 mM NaCitrate, 90 mM Alanine, 3% Trehalose, 0.01% Tween 80 | 0.01 | 3 | 132 |
| 11 | 17 | 30 mg/mL | 20 mM NaCitrate, 50 mM Alanine, 6% Trehalose, 0.1% Tween 80 | 0.1 | 6 | 795 |
| 12 | 17 | 60 mg/mL | 20 mM NaCitrate, 50 mM Alanine, 10% Trehalose, 0.1% Tween 80 | 0.1 | 10 | 660 |
| 13 | 17 | 60 mg/mL | 20 mM NaCitrate, 50 mM Alanine, 10% Trehalose, 0.1% Tween 80 | 0.1 | 10 | 660 |
| 14 | 17 | 90 mg/mL | 20 mM NaCitrate, 50 mM Alanine, 10% Trehalose, 0.1% Tween 80 | 0.1 | 10 | 440 |
| 15 | 19 | 10 mg/ml | 20 mM NaCitrate, 90 mM Alanine, 3% Trehalose, 0.1% Tween 80 | 0.1 | 3 | 1196 |
| 16 | 19 | 10 mg/ml | 20 mM NaCitrate, 90 mM Alanine, 3% Trehalose, 0.01% Tween 80 | 0.01 | 3 | 1196 |
| 17 | 19 | 20 mg/ml | 20 mM NaCitrate, 90 mM Alanine, 3% Trehalose, 0.1% Tween 80 | 0.1 | 3 | 594 |
| 18 | 19 | 20 mg/ml | 20 mM NaCitrate, 90 mM Alanine, 3% Trehalose, 0.01% Tween 80 | 0.01 | 3 | 594 |
| 19 | 19 | 30 mg/ml | 20 mM NaCitrate, 90 mM Alanine, 3% Trehalose, 0.1% Tween 80 | 0.1 | 3 | 395 |
| 20 | 19 | 30 mg/ml | 20 mM NaCitrate, 90 mM Alanine, 3% Trehalose, 0.01% Tween 80 | 0.01 | 3 | 395 |
| 21 | 19 | 20 mg/mL | 20 mM NaCitrate, 50 mM Alanine, 6% Trehalose, 0.1% Tween 80 | 0.1 | 6 | 1195 |
| 22 | 19 | 20 mg/mL | 20 mM NaCitrate, 50 mM Alanine, 6% Trehalose, 0.1% Tween 80 | 0.1 | 6 | 1195 |
| 23 | 19 | 30 mg/mL | 20 mM NaCitrate, 50 mM Alanine, 6% Trehalose, 0.1% Tween 80 | 0.1 | 6 | 795 |
| 24 | 17 and 19 | 20 mg/mL | 20 mM NaCitrate, 90 mM Alanine, 3% Trehalose, 0.01% Tween 80 | 0.1 | 3 | 594 |
| 25 | 17 and 19 | 20 mg/mL | 20 mM NaCitrate, 90 mM Alanine, 3% Trehalose, 0.01% Tween 80 | 0.01 | 3 | 594 |
| 26 | 17 and 19 | 40 mg/mL | 20 mM NaCitrate, 90 mM Alanine, 3% Trehalose, 0.1% Tween 80 | 0.1 | 3 | 304 |
| 27 | 17 and 19 | 40 mg/mL | 20 mM NaCitrate, 90 mM Alanine, 3% Trehalose, 0.01% Tween 80 | 0.01 | 3 | 304 |
| 28 | 17 and 19 | 60 mg/mL | 20 mM NaCitrate, 90 mM Alanine, 3% Trehalose, 0.1% Tween 80 | 0.1 | 3 | 198 |
| 29 | 17 and 19 | 60 mg/mL | 20 mM NaCitrate, 90 mM Alanine, 3% Trehalose, 0.01% Tween 80 | 0.01 | 3 | 198 |
| 30 | 17 and 19 | 20 mg/mL | 20 mM NaCitrate, 50 mM Alanine, 6% Trehalose, 0.1% Tween 80 | 0.1 | 6 | 1195 |
| 31 | 17 and 19 | 20 mg/mL | 20 mM NaCitrate, 50 mM Alanine, 6% Trehalose, 0.1% Tween 80 | 0.1 | 6 | 1195 |
| 32 | 17 and 19 | 40 mg/mL | 20 mM NaCitrate, 50 mM Alanine, 6% Trehalose, 0.1% Tween 80 | 0.1 | 6 | 612 |

| Example | Conc. mAb (mg/mL) | Formulation | % Tween 80 | % Trehalose | Molar Ratio Tre:mAb |
|---|---|---|---|---|---|
| 33 | 17 and 19 | 40 mg/mL | 20 mM NaCitrate, 50 mM Alanine, 10% Trehalose, 0.1% Tween 80 | 0.1 | 10 | 1015 |

Results of the stability of examples 4-32 after 3 months was as follows:

| | % Monomer Manual Integration (12 wks) | SDS-PAGE Non-reduced % Major Band(s) (135~175 KDa) | SDS-PAGE Reduced (% MW4 (Heavy) + % MW5 (Light)) |
|---|---|---|---|
| +++ | >88% | >86% | >95% |
| ++ | 86%~88% | 81%~86% | 89~95% |
| + | <86% | <81% | <89% |

| Example | Temp (° C.) | % Monomer Manual Integration (12 wks) | SDS-PAGE NR (12 wks)[1] | SDS-PAGE Reduced (12 wks)[1] |
|---|---|---|---|---|
| 5 | 5 | +++ | +++ | +++ |
| | 25 | +++ | +++ | +++ |
| | 40 | ++ | +++ | ++ |
| 6 | 5 | +++ | +++ | +++ |
| | 25 | +++ | +++ | +++ |
| | 40 | +++ | +++ | +++ |
| 7 | 5 | +++ | ++ | +++ |
| | 25 | +++ | +++ | +++ |
| | 40 | ++ | + | ++ |
| 8 | 5 | +++ | +++ | +++ |
| | 25 | +++ | +++ | +++ |
| | 40 | ++ | ++ | + |
| 9 | 5 | +++ | +++ | +++ |
| | 25 | +++ | +++ | +++ |
| | 40 | + | ++ | +++ |
| 10 | 5 | +++ | +++ | +++ |
| | 25 | +++ | +++ | +++ |
| | 40 | ++ | +++ | +++ |
| 11 | 5 | +++ | +++ | +++ |
| | 25 | +++ | +++ | +++ |
| | 40 | + | ++ | +++ |
| 12 | 5 | +++ | +++ | +++ |
| | 25 | +++ | +++ | +++ |
| | 40 | + | ++ | +++ |
| 13 | 5 | +++ | +++ | +++ |
| | 25 | +++ | +++ | +++ |
| | 40 | + | + | +++ |
| 14 | 5 | +++ | +++ | +++ |
| | 25 | +++ | +++ | +++ |
| | 40 | + | ++ | +++ |
| 15 | 5 | +++ | +++ | +++ |
| | 25 | +++ | +++ | +++ |
| | 40 | + | +++ | ++ |
| 16 | 5 | +++ | +++ | +++ |
| | 25 | +++ | +++ | +++ |
| | 40 | ++ | +++ | ++ |
| 17 | 5 | +++ | +++ | +++ |
| | 25 | +++ | +++ | +++ |
| | 40 | ++ | ++ | ++ |
| 18 | 5 | +++ | +++ | +++ |
| | 25 | +++ | +++ | +++ |
| | 40 | ++ | +++ | + |
| 19 | 5 | +++ | +++ | +++ |
| | 25 | +++ | +++ | +++ |
| | 40 | + | ++ | ++ |
| 20 | 5 | +++ | +++ | +++ |
| | 25 | +++ | +++ | +++ |
| | 40 | ++ | +++ | + |
| 21 | 5 | +++ | +++ | +++ |
| | 25 | +++ | +++ | +++ |
| | 40 | + | ++ | ++ |
| 22 | 5 | +++ | +++ | +++ |
| | 25 | +++ | +++ | +++ |
| | 40 | + | ++ | ++ |
| 23 | 5 | +++ | +++ | +++ |
| | 25 | +++ | +++ | +++ |
| | 40 | + | + | + |
| 24 | 5 | +++ | +++ | +++ |
| | 25 | +++ | +++ | +++ |
| | 40 | +++ | + | +++ |
| 25 | 5 | +++ | +++ | +++ |
| | 25 | +++ | +++ | +++ |
| | 40 | +++ | + | +++ |
| 26 | 5 | +++ | +++ | +++ |
| | 25 | +++ | +++ | +++ |
| | 40 | ++ | +++ | +++ |
| 27 | 5 | +++ | +++ | +++ |
| | 25 | +++ | +++ | +++ |
| | 40 | +++ | + | +++ |
| 28 | 5 | +++ | ++ | +++ |
| | 25 | +++ | +++ | +++ |
| | 40 | ++ | + | +++ |
| 29 | 5 | +++ | +++ | +++ |
| | 25 | +++ | +++ | +++ |
| | 40 | ++ | + | +++ |
| 30 | 5 | +++ | +++ | +++ |
| | 25 | +++ | +++ | +++ |
| | 40 | ++ | +++ | +++ |
| 31 | 5 | +++ | +++ | +++ |
| | 25 | +++ | +++ | +++ |
| | 40 | ++ | +++ | +++ |
| 32 | 5 | +++ | +++ | +++ |
| | 25 | +++ | +++ | +++ |
| | 40 | ++ | ++ | +++ |
| 33 | 5 | +++ | +++ | +++ |
| | 25 | +++ | +++ | +++ |
| | 40 | ++ | + | +++ |

The three month stability data above shows that some 40° C. formulations of 17 and 19 in combination fared as well or better than similar formulations of 17 or 19 alone.

Following the term "about" used to described amounts herein, the precise amount following the term "about" is also contemplated in each instance. All publications, patents, and patent applications cited herein are specifically incorporated herein by reference.

The invention claimed is:

1. An antibody formulation comprising:
   a) at least 10 mg/ml of one or more antibodies or fragments thereof that specifically bind to an HBV antigen
   wherein at least one of said antibodies or antibody fragments comprises a variable light (VL) domain having the amino acid sequence of SEQ ID NO. 1 and a variable heavy (VH) domain having the amino acid sequence of SEQ ID NO. 2; and
   at least a second of said antibodies or antibody fragments comprises a variable light (VL) domain having the amino acid sequence of SEQ ID NO. 3 and a variable heavy (VH) domain having the amino acid sequence of SEQ ID NO. 4;
   b) alanine at a concentration of 90 mM;
   c) sodium citrate at a concentration of 20 mM;
   d) polysorbate 80 at a concentration of 0.1%; and
   e) trehalose at a concentration of 3%.

2. The formulation of claim 1, wherein the formulation has a pH in the range between about 5.0 to 7.5.

3. The formulation of claim 1, wherein at least one of the antibodies or antibody fragments is at a concentration of at least 20 mg/ml.

4. The formulation of claim 1, wherein at least one of the antibodies or antibody fragments is at a concentration of at least 100 mg/ml.

5. The formulation of claim 1, wherein at least one of the antibodies or antibody fragments that specifically binds to an HBV antigen is stable at room temperature for at least 6 months as determined by HPSEC.

6. The formulation of claim 1, wherein at least one of the antibodies or antibody fragments that specifically binds to an HBV antigen is stable at 4° C. for at least 2 years as determined by HPSEC.

7. The formulation of claim 1, wherein less than 10% of the antibodies or antibody fragments form an aggregate as measured by HPSEC.

8. A pharmaceutical unit dosage form suitable for parenteral administration to a human which comprises
   an antibody formulation of claim 1 in a pharmaceutically suitable container.

9. The pharmaceutical unit dosage form of claim 8, wherein at least one of the said antibodies or fragments thereof has a concentration of from about 10 mg/ml to about 100 mg/ml in a volume of from 1 ml to 20 ml.

10. The pharmaceutical unit dosage form of claim 9, wherein said antibody or fragment thereof has a concentration of 80 mg/ml in a volume of 1 ml.

11. The pharmaceutical unit dosage-form of claim 9, wherein said antibody formulation is suitable for subcutaneous, intravenous, or intramuscular administration.

* * * * *